US006787686B2

(12) United States Patent
Potts et al.

(10) Patent No.: US 6,787,686 B2
(45) Date of Patent: Sep. 7, 2004

(54) *BRASSICA JUNCEA* LINES BEARING ENDOGENOUS EDIBLE OILS

(75) Inventors: Derek Arthur Potts, Saskatoon (CA); Daryl Richard Males, Saskatoon (CA); Gerhard Friedrich Werner Rakow, Saskatoon (CA); John Philip Raney, Dundurn (CA)

(73) Assignees: Saskatchewan Wheat Pool, Saskatchewan (CA); Her Majesty the Queen in right of Canada, as represented by the Minister of Agriculture and Agri-Food Canada, Ottawa (CA)

( * ) Notice: Subject to any disclaimer, the term of this patent is extended or adjusted under 35 U.S.C. 154(b) by 255 days.

(21) Appl. No.: 09/977,771

(22) Filed: Oct. 15, 2001

(65) Prior Publication Data

US 2002/0042935 A1 Apr. 11, 2002

Related U.S. Application Data

(63) Continuation of application No. 09/190,183, filed on Nov. 12, 1998, now Pat. No. 6,303,849.

(51) Int. Cl.[7] .................................................. A01H 5/00
(52) U.S. Cl. ........................................................ 800/306
(58) Field of Search ................................. 800/306, 260, 800/264

(56) References Cited

PUBLICATIONS

Raney et al, Proc. 9th Int. Rapeseed Congress, Cambridge, U.K., vol. 2: 413–415, 1995.*
Woods et al, Can. J. Plant Sci. 71: 195–198, Jan. 1991.*

* cited by examiner

*Primary Examiner*—Elizabeth F. McElwain
(74) *Attorney, Agent, or Firm*—Quarles & Brady LLP

(57) ABSTRACT

Novel lines of *Brassica juncea* yield an edible oil that has properties similar to canola oil. More specifically, the oil has an oleic acid content of at least 55% by weight, a linoleic acid content of less than 25% by weight, a linolenic acid content of less than 14% by weight, a erucic acid content of less than 1% by weight, a palmitic acid content of less than 6% by weight, a stearic acid content of less than 2.5% by weight, and a total saturated acid content of less than 7.1% by weight. The novel lines of *B. juncea* plant have a lineage that includes both lines J90-3450 and J90-4316, these being known lines of *B. juncea*, and may be formed by conventional cross fertilization or other means. The novel lines can be grown in harsher environments than conventional canola species and are high-yielding and disease-resistant.

2 Claims, 1 Drawing Sheet

BRASSICA JUNCEA LINES BEARING ENDOGENOUS EDIBLE OILS

CROSS REFERENCES TO RELATED APPLICATIONS

This application is a continuation of U.S. Ser. No. 09/190,183 filed Nov. 12, 1998 now U.S. Pat. No. 6,303,849.

FIELD OF THE INVENTION

The present invention relates to oilseeds and oilseed plants capable of producing edible oils suitable for human consumption. More particularly, the invention relates to such seeds and plants capable of producing oils having desirable characteristics similar to those of canola oil, to processes of forming such plants, and to the resulting edible oils.

BACKGROUND OF THE INVENTION

Brassica napus and Brassica rapa (campestris) are known as the canola species most effective for the production of edible oils for human consumption. These species set the benchmark in North America for Brassica oilseeds destined for the edible oil market. A Brassica oil of desirable quality must be of canola quality and contain no more than 2% by weight of the total fatty acids as erucic acid and no more than 30 μmoles of aliphatic glucosinolates in the oil-free meal. The aliphatic glucosinolates of the meal can be any one or a mixture of 3-butenyl, 4-pentenyl, 2-hydroxy-3-butenyl or 2-hydroxy-4-pentenyl glucosinolate.

Canola was developed as an edible oil crop during the 1970's by genetic alteration of rapeseed. Traditional rapeseed oil contains 25–45% by weight erucic acid and rapeseed meal contains 100–150 μmoles of glucosinolates per gram, and is still grown and utilized as an edible oil and animal feed ingredient in a number of countries, primarily China and India. Lowering the erucic acid/glucosinolate levels to create canola led to the widespread use of the oil as a salad and frying oil and in the manufacture of margarine, shortening and other food products. In addition, the meal byproduct derived during the processing of canola seed is used as a high-protein feed ingredient in rations of poultry, swine, cattle and fish.

Canola oil has a fatty acid composition that is considered to be superior to many other vegetable oils for human nutrition (McDonald, 1995 [10]—please see the References section at the end of this description for full details of referenced articles). Canola is low in saturated fat, which has been shown to increase blood cholesterol levels and lead to increased risk of heart disease. Canola oil is high (55–60% by weight) in the mono-unsaturated fatty acid, oleic acid (C-18:1). Oleic acid has been shown to reduce serum cholesterol levels and is therefore desirable in an edible oil. An oil high in mono-unsaturated fat is more stable than an oil that is high in poly-unsaturated fatty acids, such as linoleic (C-18:2) and linolenic (C-18:3) (Eskin et al., 1989 [5]). Poly-unsaturated fatty acids are more easily oxidized during cooking, which creates off-flavours in the oil. Oxidation also reduces the shelf life of the oil.

The growing conditions of the Canadian Prairies are particularly suited to the cultivation of Brassica juncea, with approximately 50,000 hectares (ha) gown annually in this region of western Canada (Woods et al. [17]). However, this species of Brassica is grown to supply condiment mustard worldwide, and does not naturally produce an oilseed having a fatty acid content suitable for the production of an edible oil product. Specifically, oilseed of Brassica juncea naturally contain approximately 25% by weight of erucic acid and 100 μmoles glucosinolates per gram of whole seed.

The main aliphatic glucosinolate in B. juncea grown as condiment mustard is 3-propenyl (allyl) glucosinolate, which is known to give mustard seed its hot and bitter taste. Further, the breakdown of this glucosinolate results in the formation of allyl isothiocyanate, which is believed to have detrimental effects on health (Ames, 1983 [2]).

Despite these characteristics, cultivars of B. juncea have been suggested as a potential source of edible oils on the basis of their improved resiliency and productivity over existing canola species. Specifically, cultivars of B. juncea are generally known to be high yielding, tolerant to both heat and drought, and disease resistant. Most particularly, B. juncea has shown superior resistance to important canola diseases such as blackleg. Some cultivars of B. juncea have also displayed resistance to pod shattering (Woods et al. 1991 [17]). Accordingly, the development of a canola-quality cultivar of B. juncea would help to increase and stabilize canola production, especially in hot, drought-prone regions.

Low erucic acid B. juncea germplasm was first identified in Australia (Kirk and Oram, 1981 [7]). These lines were designated as Zem 1 and Zem 2 and were released to plant breeders. Agriculture and Agri-Food Canada (AAFC) initiated a plant breeding program in 1985 to develop B. juncea canola, using the Zem lines as a starting point.

Researchers at AAFC developed a low glucosinolate line using an interspecific cross with a low-glucosinolate B. rapa line (Love et al., 1990 [8]). A line designated 1058 was developed that had less than 10 μmoles of total glucosinolates per gram of meal, but had very low fertility, low oil content and high erucic acid content. This initial line was improved upon and lines were developed with improved yield, higher oil content and low erucic acid content (Love et al., 1991 [9]; Rakow et al., 1995 [12]).

Low erucic acid B. juncea lines developed in Australia and by AAFC were more unsaturated (containing more linoleic and linolenic acid) than canola cultivars of B. napus or B. rapa. Oil of these lines is considered to be of lower quality than normal canola, and therefore difficult to integrate into the mainstream canola crop (Raney et al., 1995 [13]).

Researchers have attempted to alter the fatty acid profile of B. juncea through interspecific crosses. Raney et al. (1995) [13] crossed low erucic B. juncea with low linolenic B. napus. A single backcross to B. juncea was made and plants were selfed (self-fertilized). In $F_4$ generation seed, the highest oleic value was 53.7% by weight, and the saturated fat level was 9.7% by weight (palmitic and stearic). This fatty acid profile would be unacceptable as canola. Nevertheless, all generations from the backcross had depressed fertility and poor seed set, indicating that there was genetic instability as a result of the interspecific cross.

Agnihotri et al. (1995) [1] derived lines from a cross of (Eruca sativa×B. rapa)×B. juncea. One line was reported to have an oleic content of 61.9% by weight; however, this line had 103.4 μmoles of allyl glucosinolate per gram of meal, so it would not be considered to be canola quality. As described, the genetic makeup of this line was only 50% B. juncea and the generation was not specified, so genetic stability was not proven. It is highly unlikely that an interspecific line such as this would have good fertility and all of the agronomic characteristics associated with B. juncea.

International Patent Application PCT/US96/02620 to Pioneer Hi-Bred International, Inc., (published on Sep. 12, 1996 under International Publication No. WO 96/27285) discusses the potential use of a *B. napus* line to produce *B. juncea* that is low in linolenic acid, high in oleic acid and low in saturated fatty acids. Evidence of a *B. juncea* plant with an altered fatty acid profile produced by this or any other means is totally absent. No claim in the application refers to *B. juncea*.

Despite all these efforts, the need remains for a *B. juncea* line which displays superior agronomic qualities and produces an endogenous oil with an acceptable level of oleic acid (at least 55% by weight), which is low in erucic acid (less than 2% by weight), low in saturated fat (the total of C-16:0, C-18:0, C-20:0 and C-22:0 less than 7.1% by weight), low in total aliphatic glucosinolates (less than 30 μmoles per gram of meal) and low in allyl glucosinolate (less than 3 μmoles per gram of meal). To be useful, the line must be genetically stable, must have acceptable agronomic performance compared to current canola species and must have retained the positive attributes of *B. juncea*, such as adaptation to a semi-arid environment and resistance to blackleg.

SUMMARY OF THE INVENTION

An object of the present invention is to provide a line of *Brassica juncea*, and the resulting oilseeds, that satisfies the above requirements to acceptable extents.

Another object of the invention is to provide a process of producing such lines of *Brassica juncea*.

Another object of the present invention to provide a novel mature *B. juncea* oilseed capable of yielding an edible endogenous vegetable oil having a distribution of fatty acids that would be accepted as a canola equivalent oil following simple crushing and extraction.

Yet another object of the present invention to provide a novel *B. juncea* plant having satisfactory agronomic characteristics which upon self-pollination is capable of yielding an endogenous vegetable oil having a distribution of fatty acids that would be acceptable as a canola equivalent oil following simple crushing and extraction.

It is another object of the present invention to provide an edible vegetable oil extracted from *B. juncea* seeds that meets the major specifications for canola oil, as listed in Food Chemicals Codex (1996) and as required by the Canadian canola industry.

It is a further object of the present invention to provide a process for the formation of genetically stable, agronomically adapted *B. juncea* cultivars, wherein the distribution of the major fatty acids meets the specifications for canola oil as listed in Food Chemicals Codex (1996).

According to one aspect of the invention, there is provided an oilseed of the species *Brassica juncea* bearing an endogenous oil having an oleic acid content of at least 55% by weight, a linoleic acid content of less than 25% by weight, a linolenic acid content of less than 14% by weight, a erucic acid content of less than 1% by weight, a palmitic acid content of less than 6% by weight, a stearic acid content of less than 2.5% by weight, and a total saturated fatty acid content of less than 7.1% by weight.

According to another aspect of the invention, there is provided a genetically stable plant of the species *B. juncea* that develops mature seeds bearing an endogenous oil having an oleic acid content of at least 55% by weight, a linoleic acid content of less than 25% by weight, a linolenic acid content of less than 14% by weight, a erucic acid content of less than 1% by weight, a palmitic acid content of less than 6% by weight, a stearic acid content of less than 2.5% by weight, and a total saturated acid content of less than 7.1% by weight; or a part or precursor of said plant.

According to another aspect of the invention, there is provided a seed oil having an oleic acid content of at least 55% by weight, a linoleic acid content of less than 25% by weight, a linolenic acid content of less than 14% by weight, a erucic acid content of less than 1% by weight, a palmitic acid content of less than 6% by weight, a stearic acid content of less than 2.5% by weight, and a total saturated acid content of less than 7.1% by weight, said oil having been extracted from an oilseed of a line of the species *Brassica juncea*.

According to yet another aspect of the invention, there is provided a process of producing a genetically stable *B. juncea* plant that develops mature seeds bearing an endogenous oil having an oleic acid content of at least 55% by weight, a linoleic acid content of less than 25% by weight, a linolenic acid content of less than 14% by weight, a erucic acid content of less than 1% by weight, a palmitic acid content of less than 6% by weight, a stearic acid content of less than 2.5% by weight, and a total saturated acid content of less than 7.1% by weight, said process comprising the steps of: crossing a line of *B. juncea* having a lineage that includes J90-3450 with a *B. juncea* line having a lineage that includes J90-4316 to form F1 progeny; propagating said progeny by self-pollination or by producing doubled haploid progeny and, from resulting progeny, selecting genetically stable plants that generate seeds containing an endogenous oil that has an oleic acid value of more than 55% by weight, a linoleic value of less than 25% by weight, a linolenic acid value of less than 14% by weight, an erucic acid value of less than 1% by weight, a palmitic acid value of less than 6% by weight, a stearic acid content of less than 2.5% by weight and a total saturate content of less than 7.1% by weight.

According to yet another aspect of the invention, there is provided a process of producing a genetically stable *B. juncea* plant that develops mature seeds bearing an endogenous oil having an oleic acid content of at least 55% by weight, a linoleic acid content of less than 25% by weight, a linolenic acid content of less than 14% by weight, a erucic acid content of less than 1% by weight, a palmitic acid content of less than 6% by weight, a stearic acid content of less than 2.5% by weight, and a total saturated acid content of less than 6.5% by weight, said process comprising the steps of: crossing a line of *B. juncea* having a lineage that includes J90-3450 with a *B. juncea* line having a lineage that includes J90-4316 to form F1 progeny; propagating said progeny by a method selected from the group consisting of either self-pollination or development of doubled haploid plants; and, from resulting progeny, selecting genetically stable plants that generate seeds containing an endogenous oil that has an oleic acid value of more than 55% by weight, a linoleic value of less than 25% by weight, a linolenic acid value of less than 14% by weight, an erucic acid value of less than 1% by weight, a palmitic acid value of less than 6% by weight, a stearic acid content of less than 2.5% by weight and a total saturate content of less than 7.1% by weight; and utilizing mutagenesis to produce a plant with a low saturated fat content, crossing the low saturated plant or its progeny with a plant with >55% by weight oleic acid to produce progeny with an oleic acid value of more than 55% by weight, a linoleic value of less than 25% by weight, linolenic acid value of less than 14% by weight, an erucic acid value of less than 1% by weight, a palmitic acid value of less than 6% by weight, a stearic acid content of less than 2.5% by weight and a total saturate content of less than 6.5% by weight.

Thus, by means of the present invention, an endogenous vegetable oil extracted from *Brassica juncea* is provided which exhibits an oleic acid content of at least 55% by weight, a linoleic acid content of less than 40% by weight, a linolenic acid content of less than 14% by weight, a erucic acid content of less than 2% by weight, a palmitic acid content of less than 6% by weight, a stearic acid content of less than 2.5% by weight, and a total saturate content of less than 7.1% by weight. The oil is essentially equivalent in fatty acid composition to canola oil extracted from *B. napus* or *B. rapa*

In a preferred embodiment, *B. juncea* cultivars of the present invention also possess an aliphatic glucosinolate content of less than 30 μmoles per gram of oil-free meal. The allyl glucosinolate content is preferably less than 3 μmoles per gram of oil-free meal.

*Brassica juncea* plants are provided that are genetically stable, are morphologically recognizable as *B. juncea*, have generally the same desirable agronomic attributes as mustard-quality *B. juncea* and produce an endogenous oil that is essentially equivalent in fatty acid composition to canola oil.

A process is provided for the formation of *B. juncea* plants that produce endogenous oil that has a total saturate content of less than 6.5% by weight. This process includes the use of a mutagenic agent to produce DH plants with lower saturated fat content and then crossing said plants with high oleic *B. juncea* plants to produce a high oleic *B. juncea* plant with reduced saturated fat content.

DESCRIPTION OF THE INVENTION

Explanation of Terms

Figure 1:
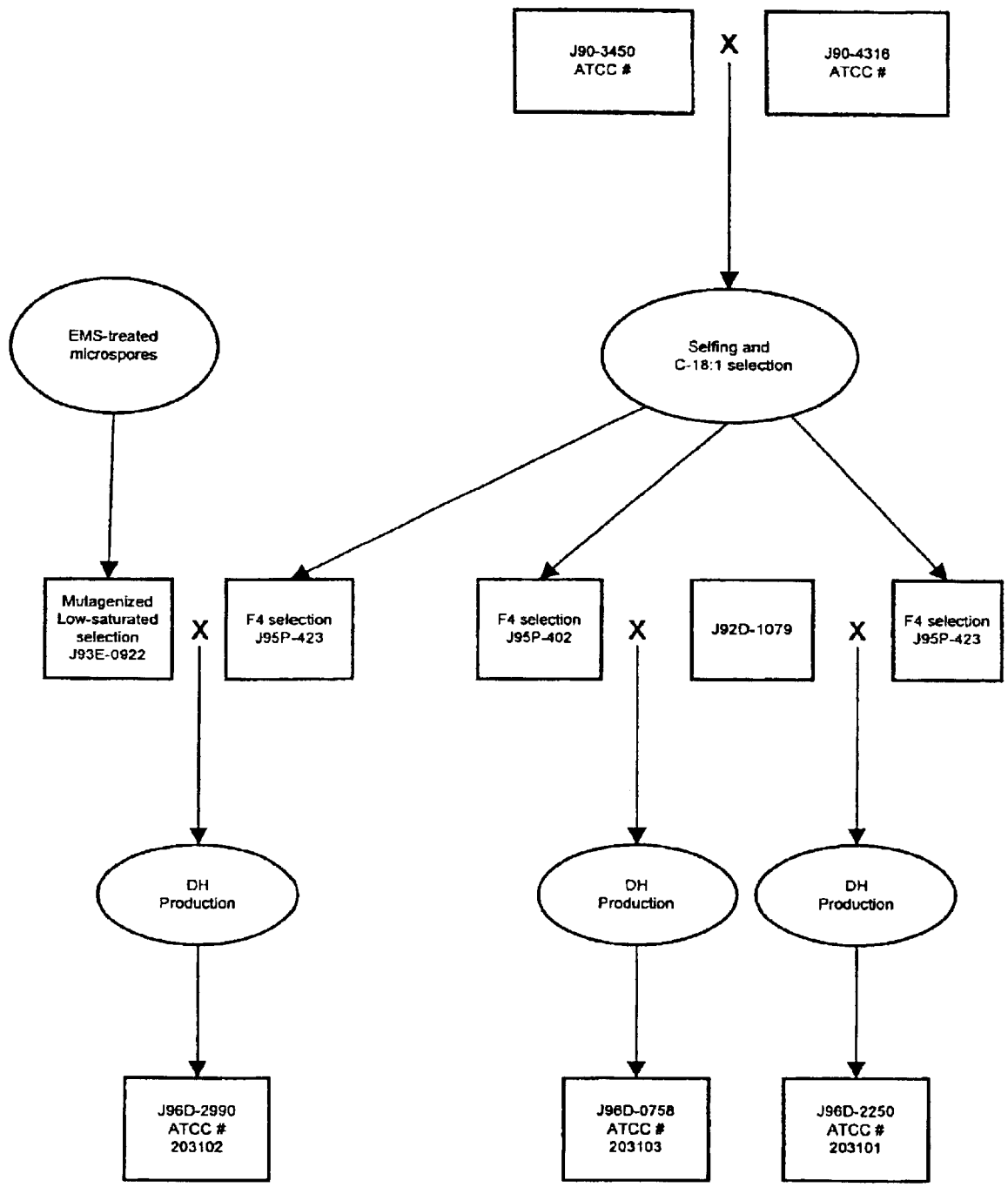
FIG. 1 is a diagrammatic representation of a preferred process used to produce examples of *B. juncea* lines of this invention.

For clarity of description, some of the terminology used herein is explained as follows.

The term "line" refers to a group of plants that displays very little overall variation among individuals sharing that designation.

A "variety" or "cultivar" is a line that is used for commercial production.

A "doubled haploid" (DH) line refers to a line created by the process of microspore embryogenesis, in which a plant is created from an individual microspore. By this process, lines are created that are homogeneous, i.e. all plants within the line have the same genetic makeup. The original DH plant is referred to as DH1, while subsequent generations are referred to as DH2, DH3 etc. Doubled haploid procedures are well known and have been established for several crops. A procedure for *B. juncea* has been described by Thiagrara-jah and Stringham (1993).

The term "high oleic" refers to *B. juncea* with an oleic acid content of more than 55% by weight.

"Total saturates" refers to the combined percentages of palmitic (C-16:0), stearic (C-18:0), arachidic (C-20:0) and behenic (C-22:0) fatty acids. The fatty acid concentrations discussed herein are determined in accordance with the standard procedure, American Oilseed Chemists' Society (AOCS) method Celd-91 (the disclosure of which is incorporated herein by reference). Fatty acid concentrations are expressed as a percentage by weight of the total fatty acid content.

"Halfseed" analysis refers to a procedure whereby fatty acid analysis is carried out on one cotyledon (halfseed) and the remaining halfseed is used to form a plant if the results of the analysis are positive.

"Mutagenesis" is a process in which an agent known to cause mutations in genetic material is applied to plant material. In the experimental work, the mutagenic agent used was ethyl methyl sulfonate (EMS). The purpose is to cause new genetic variability in a species, usually it is done with a specific trait in mind. An example of mutagenesis used on haploids to induce novel variation has been described by Swanson et al. (1988) [14]. The disclosure of this article is herein incorporated by reference.

"Regeneration techniques" involve selection of cells capable of regeneration (e.g. seeds, microspores, ovules, pollen, vegetative parts) from a selected plant or variety. These cells may optionally be subjected to mutagenesis, following which a plant is developed from the cells using regeneration, fertilization, and/or growing techniques based on the types of cells mutagenized. Applicable regeneration techniques are known to those skilled in the art; see, for example, Armstrong, C. L., and Green, C. E., *Planta* 165:322–332 (1985); and Close, K. R., and Ludeman, L. A., *Planta Science* 52:81–89 (1987), the disclosures of which are incorporated herein by reference.

Seeds, Plants

It has been found that *Brassica juncea* lines according to the present invention can be created by the combination of genetic determinants that heretofore were not recognized as making possible the formation of an endogenous oil, wherein the levels of oleic acid, linoleic acid, linolenic acid, erucic and saturated fatty acids are in an atypical combination compared to known *B. juncea* cultivars. The relatively high concentration of oleic acid and low concentrations of linoleic acid and linolenic acid, combined with low concentration of saturates, provides an oil with the same desirable nutritional and processing attributes as canola oil available from existing sources.

While other researchers have attempted to attain a high oleic fatty acid content in *B. juncea* by interspecific crossing, the present invention is based on the combining of two lines of *B. juncea*. Interspecific crossing is thus avoided. This runs contrary to conventional belief that interspecific crossing or mutagenesis would be required to obtain the desired characteristics.

The ability to combine high oleic lines of this invention with low saturate lines and recover lines with both attributes was unexpected. Prior to the present invention, it would reasonably have been concluded that when a low saturate line was crossed with a high oleic line, the saturate value would increase as well as the mono-unsaturated value (oleic acid), since both require a reduction in the desaturation process. Conventional opinion suggested that it would be difficult to reduce the amount of poly-unsaturated fatty acids (c-18:2 and c-18:3) to obtain more mono-unsaturated fatty acid (c-18:1) without obtaining more of a saturated fatty acid (c-18:0). Since the biochemical pathway is from 18:0→18:1→18:2→18:3, backing up the pathway from 18:2 to 18:1 may also lead to higher 18:0. Unexpectedly, this has been shown not to be the case by the inventors of the present invention.

The parent lines used in the present invention may be combined by conventional cross-breeding or by any other known technique for combining the genetic material of different lines of the same species.

The combination of *B. juncea* plant type and agronomic performance with a canola-like fatty acid profile enables canola oil production in areas where *B. juncea* demonstrates better adaptation than the current canola species, *B. napus* and *B. rapa*.

The *B. juncea* lines of the present invention are provided in a substantially uniform stand of plants, i.e. the plants within each line are essentially similar in quality and morphological characteristics. When the plants are microspore-derived doubled-haploid plants, they are genetically homogeneous. In the following Examples, data from two generations are provided to show the genetic stability of the pertinent traits (see Table I and Table III below). The exact level of fatty acids will depend somewhat on the growing conditions. For example, in Table I and Table III, the DH2 generation, which was grown in Chile, is consistently lower in saturates than the DH3 generation grown in western Canada. However, the variation due to environment is minor in comparison to the variation due to genetic determinants.

The *B. juncea* plants of the present invention are capable of propagation in the field, particularly in areas where *B. juncea* is currently grown as a mustard crop (see Table II).

Using the plants of this present invention, and techniques available to persons skilled in the art, other desirable traits may be incorporated, such as resistance to specific herbicides, improved agronomic characteristics, or a pollination control system to enable hybrid production.

It will be readily apparent that, given the novel lines of the present invention as a starting point, the particular benefits afforded by these lines may be manipulated in a number of ways by techniques available to persons skilled in the art without departing from the scope of the present invention. Accordingly, variations of the plant lines produced by such manipulations are held to be within the scope of the present invention. For example, the seed oil profile of the novel lines may be transformed into other agronomically desirable *B. juncea* varieties by conventional plant breeding techniques involving cross-pollination and selection of the progeny. Regeneration techniques may also be used.

Using plants of the present invention, persons skilled in the art may also make interspecific crosses to varieties of *B. napus* or *B. rapa* which possess modified fatty acid profiles in order to give special properties to the oil. For example, one of the lines herein described could be crossed to a low linolenic *B. napus* variety such as Apollo to transfer the low linolenic trait to *B. juncea*. Accordingly, all such variations are held to be within the scope of the present invention.

Process

The first essential parental *B. juncea* plant is the line J90-3450, including any *B. juncea* that is derived directly or indirectly therefrom (i.e. any *B. juncea* that includes J90-3450 in its lineage) or has the same essential properties. J90-3450 was developed by AAFC. Rakow (1991) has described the development of this line and some of its attributes. Compared to J90-4316 (which is described in Table 2), J90-3450 is slightly earlier maturing and shorter. It is about 1% by weight higher in oil content, but contains a substantial amount of allyl glucosinolate. The fatty acid composition of this line is presented in Table 1.

A sample of seed of J90-3450 was deposited by Agriculture and Agri-Food Canada under the terms of the Budapest Treaty on Oct. 23, 1998 at the American Type Culture Collection of 10801 University Blvd., Manassas, Va., USA 20110-2209 under the Accession No. ATCC 203389.

The second essential *B. juncea* parent is J90-4316, including any *B. juncea* that is derived directly or indirectly therefrom (i.e. any *B. juncea* that includes J90-4316 in its lineage) or has the same essential properties. J90-4316 was developed by AAFC. Rakow (1991) has described the development of this line and some of its characteristics. The fatty acid composition of this line is presented in Table 1 and the chief agronomic attributes are presented in Table 2.

A sample of seed of J90-4316 was deposited by Agriculture and Agri-Food Canada under the terms of the Budapest Treaty on Oct. 23, 1998 at the American Type Culture Collection of 10801 University Blvd., Manassas, Va., USA 20110-2209 under the Accession No. ATCC 203390.

In accordance with the process of the present invention, a *B. juncea* plant that has a lineage that includes J90-3450 is crossed with a plant that has a lineage that includes J90-4316 to form F1 progeny. Such progeny are self-pollinated or used to produce DH plants. From the progeny of the cross, selections are made which exhibit an endogenous oil that has an oleic acid value of more than 55% by weight, a linoleic value of less than 25% by weight, a linolenic acid value of less than 14% by weight, an erucic acid value of less than 1% by weight, a palmitic acid value of less than 6% by weight, a stearic acid content of less than 2.5% by weight and a total saturate content of less than 7.1% by weight.

As noted earlier, these contents are determined according to the standard procedure of American Oilseeds Chemists' Society (AOCS) method Celd-91 (the disclosure of which is incorporated herein by reference). Briefly stated, this involves crushing the seed and extracting the oil as fatty acid methyl esters. The fatty acid methyl esters are then determined quantitatively using gas liquid chromatography in which a packed column separates the fatty acids on the basis of degree of unsaturation and chain length.

As noted above, obtaining plants with this combination of fatty acids from this process was unexpected. Prior to the present invention, neither J90-3450 nor J90-4316 was known to possess genes that conferred this beneficial composition.

In a preferred embodiment of the process, DH lines or self-pollinated, inbred lines derived from J90-3450 and J90-4316, or from the cross between them, and possessing the desired fatty acid profile, are used as parents. The DH or inbred lines will be homozygous and homogeneous and therefore the transfer of genetic determinants is much more predictable. Examples of such lines are J96D-0758 and J96D-2250, which are described in the Examples and have been deposited at the American Type Culture Collection of 10801 University Blvd., Manassas, Va., USA 20110-2209, on Aug. 11, 1998 under the terms of the Budapest treaty as ATCC #203103 and ATCC #203101 respectively.

It is important to the process that selection and testing is carried out to ensure that the progeny are genetically stable and possess morphological and agronomic characteristics associated with *B. juncea*. Testing should be done in several environments using randomized and replicated field tests, such as are described by Downey and Rakow (1987) [4]. The results of this type of testing are presented in Table 2.

In a preferred embodiment of the process, progeny are selected which have a total glucosinolate content of less than 30 μmoles per gram of oil-free meal and less than 3 μmoles of allyl glucosinolate per gram of oil-free meal. Methods of testing of glucosinolates are described by Daun and McGregor (1991) [3]. For quantification of individual glucosinolates, gas chromatography of the trimethylsiyl derivatives of desulphated glucosinolates has become the preferred method.

In another preferred embodiment of the process, microspores are subjected to treatment by ethyl methyl sulfonate (EMS) or another mutagen. A procedure for conducting microspore mutagenesis has been described by Swanson et al. (1988 [14], 1989 [15]). In the case of the present invention, microspores are exposed to EMS for 60 minutes, 48 hours after they were isolated from buds. DH lines are developed from the EMS treated microspores using standard regeneration techniques and screened for fatty acid profile. Selections are made that have lower than normal saturated fat contents. Lines with reduced saturated fat content are crossed with lines that have high oleic acid values. DH or inbred lines are produced and selected for a high oleic and reduced saturated fatty acid content.

This process provides *B. juncea* that yields endogenous oil that is essentially equivalent to canola oil, without recourse to interspecific crossing to current canola species, *B. napus* and *B. rapa*. Interspecific crossing will often cause genetic instability and may eliminate the agronomic benefits associated with *B. juncea*.

Oil

A vegetable oil extracted from *B. juncea* is provided which is generally comparable to canola oil. The reduced level of polyunsaturated fat compared to previous low erucic acid *B. juncea* oil increases the oxidative stability, thereby improving the cooking odour and shelf life of the oil. The combination of fatty acids will allow for the eventual acceptance of oil derived from *B. juncea* as canola oil. No separation of *B. juncea* seed from other canola seed will be necessary prior to oil extraction.

Specifically, an oil extracted from *B. juncea* is provided with: less than 6% by weight palmitic (C-16:0), less than 2.5% by weight stearic (C-18:0), more than 55% by weight oleic (C-18:1), less than 25% by weight linoleic (C-18:2), less than 14% by weight linolenic (C-18:3), less than 1% by weight erucic (C-22:1) acid and less than 7.1% by weight total saturated fatty acids (C-16:0+C-18:0+C-20:0+C-22:0). The iodine value (measured according to AOCS method Tz 1c-85) is generally in the range of 110–126.

The Canadian canola industry has stringent requirements for total saturates, as does the USA. To be labeled as "low in saturates" in the USA, oil must have 1 gram or less of saturates per 14 gram serving, which is equivalent to about 7.1% by weight total saturates. The *B. juncea* oil of the present invention meets this requirement.

In a preferred embodiment, endogenous oil extracted from *B. juncea* is provided with the characteristics listed above, except that the total saturated fatty acids are less than 6.5% by weight, more preferably less than 6.0% by weight. This reduction in saturated fatty acids provides greater nutritional benefits associated with lowering saturated fat content in the diet and provides greater assurance that the oil will be labelled as "low in saturates."

In another preferred embodiment, the above extracted endogenous oil also has a desirable oleic acid content of at least 60% by weight.

In yet another preferred embodiment, the meal remaining after oil extraction from *B. juncea* has an allyl glucosinolate content of less than 3 μmoles per gram and a total aliphatic glucosinolate content of less than 30 μmoles per gram.

To be useful, it is essential that the *B. juncea* from which the oil is extracted has been shown to be genetically stable and well adapted to a growing region.

The present invention is illustrated in more detail with reference to the following Examples, which should not be considered as limiting the scope of the present invention.

EXAMPLE I

The procedure used in the creation of new plant material of the present invention designated J96D-0758 was as follows. This process is illustrated in FIG. 1 of the accompanying drawings. Before continuing, it should be noted that, apart from the use of parent lines J90-3450 and J90-4316, all other lines mentioned in FIG. 1 may be replaced by lines produced from the process of the present invention and selected for similar properties. FIG. 1 is therefore merely illustrative of the general process of the invention. The lines named in FIG. 1 are those that were used to produce the lines described in these Examples.

A cross was made between two lines developed by AAFC, J90-3450 and J90-4316. Both parents are low erucic but neither line was known to possess genes that confer a high oleic content. Rakow (1991) [11] has described the development of these lines. The $F_1$ plants were selfed to produce $F_2$ seed. $F_2$ plants were grown in the field and harvested in bulk. A $F_3$ bulk population was grown in the field and individual plants were harvested. Fatty acid analysis was carried out on seed from each $F_3$ plant. Unexpectedly, plants were identified that possessed fatty acid profiles similar to *B. napus* canola. Individual seeds from these $F_3$ plants were tested by the halfseed method, in which ½ of the seed is analyzed for fatty acid profile and the other +e,fra 2+ee of the seed is grown to produce the next generation. $F_4$ plants with canola-like fatty acid profiles were identified. One such plant was designated as J95P-402. A cross was made between J95P-402 and line J92D-1079 and from this cross, microspore-derived doubled haploid (DH) lines were produced. J96D-0758 was one of the DH lines derived from this cross. The fatty acid profiles of J95P-402 and J92D-1079 and the fatty acid profiles of the DH2 and DH3 generations of J96D-0758 line are presented in Table J96D-0758 has been compared to current canola species in southern Saskatchewan and Alberta. The results presented in Table 2 indicate that this line is well adapted to this region. Seed of J96D-0758 was deposited by the Saskatchewan Wheat Pool on Aug. 11, 1998 under Accession No. ATCC 203103 at the American Type Culture Collection of 10801 University Blvd., Manassas, Va., 20110-2209, U.S.A., under the terms of the Budapest Treaty.

TABLE I

Fatty acid composition of DH2 and DH3 generations of *Brassica juncea* lines and their parents
Fatty Acid Composition (% by weight)

| Name | Generation | Palmitic Acid C-16:0 | Stearic Acid C-18:0 | Oleic Acid C-18:1 | Linoleic Acid C-18:2 | Linolenic Acid C-18:3 | Arachidic Acid C-20:0 | Behenic Acid C-22:0 | Erucic Acid C-22:1 | Saturated Fatty Acids C-16-C-22 | Iodine value |
|---|---|---|---|---|---|---|---|---|---|---|---|
| J90-3450 | | 3.7 | 2.4 | 46.1 | 33.3 | 11.6 | 0.7 | 0.3 | 0.1 | 7.1 | 132 |
| J90-4316 | | 3.9 | 2.2 | 46.9 | 31.6 | 11.3 | 0.5 | 0.3 | 0.6 | 7.0 | 129 |
| J92D-1079 | | 4.3 | 2.2 | 44.4 | 34.1 | 11.8 | 0.6 | 0.3 | 0.0 | 7.4 | 132 |
| J95P-402 | F6 | 4.4 | 2.5 | 58.6 | 20.0 | 12.3 | 0.5 | 0.3 | 0.0 | 7.7 | 120 |
| J96D-0758 | DH2 | 3.4 | 2.3 | 65.4 | 14.1 | 11.5 | 0.6 | 0.3 | 0.0 | 6.6 | |
| J96D-0758 | DH3 | 3.5 | 2.6 | 65.7 | 14.7 | 9.4 | 0.6 | 0.3 | 0.3 | 7.0 | 110 |

TABLE I-continued

Fatty acid composition of DH2 and DH3 generations of Brassica juncea lines and their parents
Fatty Acid Composition (% by weight)

| Name | Generation | Palmitic Acid C-16:0 | Stearic Acid C-18:0 | Oleic Acid C-18:1 | Linoleic Acid C-18:2 | Linolenic Acid C-18:3 | Arachidic Acid C-20:0 | Behenic Acid C-22:0 | Erucic Acid C-22:1 | Saturated Fatty Acids C-16-C-22 | Iodine value |
|---|---|---|---|---|---|---|---|---|---|---|---|
| J96D-2250 | DH2 | 3.5 | 2.3 | 64.2 | 15.0 | 11.9 | 0.6 | 0.3 | 0.0 | 6.7 | |
| J96D-2250 | DH3 | 3.7 | 2.4 | 64.5 | 15.9 | 9.9 | 0.6 | 0.3 | 0.1 | 7.0 | 112 |

TABLE II

Agronomic performance of Brassica juncea compared to B. napus and B. rapa

| Name | Species | Sites | Yield % B. napus Checks | Maturity (days) | Height (cm) | Blackleg* | Fatty Acid (% by weight) C-18:1 | Saturates | Glucosinolates (μmoles/g meal) Allyl | Aliphatic |
|---|---|---|---|---|---|---|---|---|---|---|
| AC EXCEL | B. napus | 10 | 96.6 | 85.7 | 102.8 | 52.1 | 65.2 | 6.9 | 0.3 | 11.9 |
| DEFENDER | B. napus | 10 | 96.1 | 84.8 | 103.9 | 57.4 | 64.2 | 7.1 | 0.2 | 11.1 |
| LEGACY | B. napus | 10 | 107.3 | 84.4 | 97.7 | 68.5 | 63.6 | 6.9 | 0.2 | 8.2 |
| MAVERICK | B. rapa | 10 | 105.6 | 74.4 | 96.2 | | 61.0 | 5.7 | 0.1 | 14.4 |
| AC PARKLAND | B. rapa | 10 | 107.9 | 74.8 | 96.2 | | 60.5 | 5.7 | 0.2 | 15.3 |
| REWARD | B. rapa | 10 | 114.5 | 74.8 | 90.4 | | 61.0 | 5.7 | 0.4 | 20.2 |
| J90-4316 | B. juncea | 10 | 127.5 | 83.5 | 124 | 32.6 | 46.9 | 7.0 | 3.2 | 21.7 |
| J96D-0758 | B. juncea | 10 | 111.3 | 85.7 | 119.2 | 20.0 | 65.7 | 7.0 | 2.1 | 19.9 |
| J96D-0899 | B. juncea | 10 | 120.9 | 84.2 | 127.2 | 24.8 | 61.5 | 6.9 | 1.8 | 18.9 |
| J96D-2250 | B. juncea | 7 | 115.9 | 82.1 | 132.8 | 27.8 | 64.5 | 7.0 | 2.4 | 19.4 |

*Blackleg disease rating expressed as a % of disease severity on susceptible cultivar "Westar"

EXAMPLE II

The procedure used in the creation of new plant material of the present invention designated J96D-2250 is identical to that of Example I except that the $F_4$ line J95P-423 was used instead of J95P-402 as a parent and the final cross was J92D-1079/J95P-423. J96D-2250 is a DH line produced from the $F_1$ generation of this cross.

The fatty acid profiles of the DH2 and DH3 generations of J96D-2250 are presented in Table 1. The fatty acid composition of J95P-423 is presented in Table 3. J96D-2250 has been compared to current canola species in southern Saskatchewan and Alberta. The results presented in Table 2 indicate that this line is well adapted to this region. Seed of J96D-2250 was deposited by the Saskatchewan Wheat Pool on Aug. 11, 1998 under Accession No. ATCC 203101 at the American Type Culture Collection of 10801 University Blvd., Manassas, Va., 20110-2209, U.S.A., under the terms of the Budapest Treaty.

EXAMPLE III

The procedure used in the creation of new plant material of the present invention designated J96D-2990 was as follows.

The $F_4$ line J95P-423 was developed as described in Example I and Example II.

In an attempt to alter the oleic acid content of B. juncea, mutagenesis using EMS was carried out at the microspore stage. Surviving microspores were developed into DH plants. An example of this is the line designated J93E-0922. The oleic content of this line was found to be similar to other low erucic lines, but the saturate level was unusually low. A cross was made between J95P-423 and J93E-0922 and DH plants were produced from $F_1$ donors.

It was not expected that the low saturate trait would be transferred to a high oleic type. A change in the desaturation process which causes a shift from poly-unsaturated linoleic acid to mono-unsaturated oleic acid would also be expected to cause an increase in the amount of saturated fatty acids. However, selections were made which combined high oleic with low saturate values.

The fatty acid profiles of DH2 and DH3 generations of J96D-2990 and of its parents are presented in Table III. Seed of J96D-2990 was deposited by the Saskatchewan Wheat Pool on Aug. 11, 1998 under Accession No. ATCC 203102 at the American Type Culture Collection of 10801 University Blvd., Manassas, Va., 20110-2209, U.S.A., under the terms of the Budapest Treaty.

TABLE III

Fatty Acid Composition of line J96D-2990 and its parents
Fatty Acid Composition (% by weight)

| Name | Generation | Palmitic Acid C-16:0 | Stearic Acid C-18:0 | Oleic Acid C-18:1 | Linoleic Acid C-18:2 | Linolenic Acid C-18:3 | Arachidic Acid C-20:0 | Behenic Acid C-22:0 | Erucic Acid C-22:1 | Saturated Fatty Acids C-16-c-22 | Iodine value | N |
|---|---|---|---|---|---|---|---|---|---|---|---|---|
| J95P-423 | F5 | 4.2 | 2.5 | 62.5 | 16.2 | 11.4 | 0.6 | 0.3 | 0.0 | 7.5 | 113 | 2 |
| J93E-0922 | DH3 | 3.4 | 1.9 | 47.5 | 31.6 | 13.0 | 0.4 | 0.2 | 0.2 | 5.9 | 130 | 2 |

TABLE III-continued

Fatty Acid Composition of line J96D-2990 and its parents
Fatty Acid Composition (% by weight)

| Name | Generation | Palmitic Acid C-16:0 | Stearic Acid C-18:0 | Oleic Acid C-18:1 | Linoleic Acid C-18:2 | Linolenic Acid C-18:3 | Arachidic Acid C-20:0 | Behenic Acid C-22:0 | Erucic Acid C-22:1 | Saturated Fatty Acids C-16-c-22 | Iodine value | N |
|---|---|---|---|---|---|---|---|---|---|---|---|---|
| J96D-2990 | DH2 | 3.1 | 1.7 | 65.2 | 14.9 | 12.2 | 0.5 | 0.2 | 0.0 | 5.5 | | 1 |
| J96D-2990 | DH3 | 3.5 | 1.7 | 66.0 | 14.2 | 11.8 | 0.5 | 0.2 | 0.0 | 5.9 | 115 | 2 |

EXAMPLE IV

This example describes the oil produced from *B. juncea* lines derived from the processes described in Example I and Example II and from other *B. juncea* lines selected using the same essential process.

Six DH lines derived from the same crosses as those described in Examples I and II were bulked together to provide seed for pilot scale oilseed crushing. About 740 kg of seed was degummed, alkali refined, bleached and deodorized to produce refined, bleached and deodorized oil. Data in Table IV demonstrate that the *B. juncea* oil meets the critical specifications outlined in Food Chemicals Codex (1996) for canola oil. The *B. juncea* oil of the present invention also meets the more rigorous requirements of the Canadian canola industry, which specifies that canola-quality *B. juncea* will have to have a minimum oleic acid content of 55% by weight. The *B. juncea* oil can be blended with canola oil from other sources without any loss of nutritional value and without any change in functional properties.

TABLE IV

Food Chemicals Codex (1996) specifications for canola oil and data obtained for refined-bleached-deodorized oil derived from *B. juncea*.

| Property | Canola | *B. juncea* |
|---|---|---|
| Fatty Acids, weight % by weight | | |
| <14 | <0.1 | 0.0 |
| 14:0 | <0.2 | 0.1 |
| 16:0 | <6.0 | 3.7 |
| 16:1 | <1.0 | 0.2 |
| 18:0 | <2.5 | 2.3 |
| 18:1 | >50.0 | 59.3 |
| 18:2 | <40.0 | 20.0 |
| 18:3 | <14.0 | 11.2 |
| 20:0 | <1.0 | 0.7 |
| 20:1 | <2.0 | 1.5 |
| 22:0 | <0.5 | 0.3 |
| 22:1 | <2.0 | 0.1 |
| 24:0 | <0.2 | 0.3 |
| 24:1 | ≦0.2 | 0.3 |
| Acid value | ≦6 | 0.03 |
| Cold Test | Passes test | Pass |
| Colour (AOCS-Wesson) | ≦1.5R/15Y | 1.1R/7.4Y |
| Erucic acid | ≦2.0% by weight | 0.1 |
| Free fatty acids (as oleic) | ≦0.05% by weight | 0.01 |
| Heavy metals (as Pb) | ≦5 mg/kg | <1.50 |
| Iodine value | 110–126 | 115.3 |
| Lead | <0.1 mg/kg | <0.1 |
| Linolenic acid | ≦14.0% by weight | 11.2 |
| Peroxide value | ≦10 meq/kg | 2.03 |
| Refractive index | 1.465–1.467 | 1.4657 |
| Saponifiable value | 178–193 | 188 |
| Stability | ≧7 h | 13 |
| Sulfur | ≦10 mg/kg | 1.36 |
| Unsaponifiable matter | ≦1.5% by weight | 0.82 |
| Water | ≦0.1% by weight | 0.0 |

REFERENCES

1. Agnihotri, A., Kaushik, N., Singh, N. K., Raney, J. P. and Downey, R. K. 1995. Selection for better agronomical and nutritional characteristics in Indian rapeseed-mustard. Proc. $9^{th}$ Int. Rapeseed Cong., Cambridge, U.K. Vol. 2: 425–427.
2. Ames, B. N. 1983. Dietary carcinogens and anticarcinogens. Science 221: 1256–1264.
3. Daun, J. K. and McGregor, D. I. 1991. Glucosinolates in seeds and residues. In: Analysis of Oilseeds, Fats and Fatty foods. J. B. Rossell and J. L. R. Pritchard, eds. Elsevier Applied Science, London, pp. 185–226.
4. Downey, R. K. and Rakow, G. F. W. 1987. Rapeseed and mustard. In: Principles of cultivar development. W. R. Fehr, ed. Macmillian, NY. Pp. 437–486.
5. Eskin, N. A. M., Vaisey-Genser, M., Durance-Todd, S. and Przybylski, R. 1989. Stability of low linolenic acid canola oil to frying temperatures. J. Amer. Oil Chem. Soc. 66: 1081–1084.
6. Food Chemicals Codex. 1996. $4^{th}$ Edition. Committee on Food Chemicals Codex, Food and Nutrition Board, Institute of Medicine, National Academy of Sciences. National Academy Press, Washington. pp. 77–79.
7. Kirk, J. T. O. and Oram, R. N. 1981. Isolation of erucic acid free lines of *Brassica juncea*: Indian mustard now a potential oilseed crop in Australia. J. Aust. Inst. Agric. Sci. 47: 51–52.
8. Love, H. K., Rakow, G., Raney, J. P. and Downey, R. K. 1990. Development of low glucosinolate mustard. Can. J. Plant Sci. 70:419–424.
9. Love, H. K., Rakow, G., Raney, J. P. and Downey, R. K. 1991. Breeding improvements towards canola quality *Brassica juncea*. Proc. $8^{th}$ Int. Rapeseed Congress, Saskatoon, Canada. Vol. 1: 164–169.
10. McDonald, B. E. 1995. Oil properties of importance in human nutrition. In: Brassica Oilseeds: Production and Utilization. D. S. Kimber and D. I. McGregor, eds., CAB International, Oxon, U.K., pp. 291–299.
11. Rakow, G. 1991. Canola quality mustard. Proc. Special Cropportunities 1: A conference organized by the Crop Development Centre and the Extension Division, University of Saskatchewan, Saskatoon, Canada. pp. 55–59.
12. Rakow, G., Raney, J.P. and Males, D. 1995. Field performance of canola quality *Brassica juncea* Proc. 9th Int. Rapeseed Congress, Cambridge, U.K. Vol. 2: 428–430.
13. Raney, P., Rakow, G. and Olson, T. 1995. Development of zero erucic, low linolenic *Brassica juncea* utilizing interspecific crossing. Proc. $9^{th}$ Int. Rapeseed Congress, Cambridge, U.K. Vol. 2: 413–415.
14. Swanson, E. B., Coumans, M. P., Brown, G. L., Patel, J. D. and Beversdorf, W. D. 1988. The characterization of herbicide tolerant plants in *Brassica napus* L. after in vitro selection of microspores and protoplasts. Plant Cell Rep. 7: 83–87.
15. Swanson, E. B., Herrgesell, M. J., Arnoldo, M., Sippell, D. W. and Wong, R. S. C. 1989. Microspore mutagenesis and selection: canola plants with field tolerance to the imidazolinones. Theor. Appl. Genet. 78: 525–530.
16. Thiagarajah, M. R. and Stringham, G. R. 1993. A comparison of genetic segregation in traditional and microspore-derived populations of *Brassica juncea* L. Czem and Coss. Plant Breeding 111: 330–334.
17. Woods, D. L., Capcara, J. J. and Downey, R. K. 1991. The potential of mustard (*Brassica juncea* (L.) Coss) as an edible oil crop on the Canadian Prairies. Can. J. Plant Sci. 71: 195–198.

The disclosures of the above articles are specifically incorporated herein by reference.

What we claim is:

1. An oil seed of *B. juncea* selected from the group consisting of line J96D-2250 (ATCC Accession No. 203101) and line J96D-0758 (ATCC Accession No. 203103).

2. A plant grown from an oilseed of *B. juncea* as defined in claim 1, or having the physiological characteristics such a plant.

* * * * *